(12) United States Patent
Stubkjaer et al.

(10) Patent No.: US 12,083,302 B2
(45) Date of Patent: Sep. 10, 2024

(54) DUAL PUMP ARTHROSCOPIC IRRIGATION/ASPIRATION SYSTEM WITH OUTFLOW CONTROL

(71) Applicant: Conmed Corporation, Utica, NY (US)

(72) Inventors: Eric Stubkjaer, Gulfport, FL (US); David D. Blight, Largo, FL (US); Peter C. Miller, Largo, FL (US); Karl W. Guenther, Palm Harbor, FL (US)

(73) Assignee: Conmed Corporation, Utica, NY (US)

( * ) Notice: Subject to any disclaimer, the term of this patent is extended or adjusted under 35 U.S.C. 154(b) by 0 days.

(21) Appl. No.: 18/182,888

(22) Filed: Mar. 13, 2023

(65) Prior Publication Data
US 2023/0211069 A1 Jul. 6, 2023

Related U.S. Application Data

(62) Division of application No. 16/448,141, filed on Jun. 21, 2019, now Pat. No. 11,602,590, which is a
(Continued)

(51) Int. Cl.
*A61M 3/02* (2006.01)
*A61M 1/00* (2006.01)
*A61M 39/28* (2006.01)

(52) U.S. Cl.
CPC ............ *A61M 3/0258* (2013.01); *A61M 1/72* (2021.05); *A61M 1/74* (2021.05); *A61M 1/77* (2021.05); *A61M 1/772* (2021.05); *A61M 3/0201* (2021.05); *A61M 3/0202* (2021.05); *A61M 3/0208* (2014.02); *A61M 3/0212* (2014.02); *A61M 3/0216* (2014.02); *A61M 3/022* (2014.02); *A61M 39/28* (2013.01); *A61M 1/80* (2021.05); *A61M 2205/12* (2013.01);
(Continued)

(58) Field of Classification Search
CPC ............ A61M 1/74; A61M 1/71; A61M 1/72; A61M 1/73; A61M 1/75; A61M 1/76; A61M 1/77; A61M 1/772; A61M 1/774; A61M 1/777; A61M 1/80; A61M 3/0258; A61M 3/0202; A61M 39/28; A61M 2039/1044; A61M 2205/12; A61M 2205/3331; A61M 2205/3344
See application file for complete search history.

(56) References Cited

U.S. PATENT DOCUMENTS

| | | | | |
|---|---|---|---|---|
| 5,630,799 A | * | 5/1997 | Beiser | A61B 17/320016 604/67 |
| 6,176,847 B1 | * | 1/2001 | Humphreys, Jr. | A61M 3/0208 604/246 |
| 2005/0095155 A1 | * | 5/2005 | Blight | A61M 3/0201 417/477.13 |

\* cited by examiner

*Primary Examiner* — Kami A Bosworth
*Assistant Examiner* — Avery Smale
(74) *Attorney, Agent, or Firm* — Bond, Schoeneck & King, PLLC; Frederick J. M. Price

(57) ABSTRACT

A fluid pump system having a first fluid pump for pumping fluid from a source to a surgical site and a second fluid pump for removing fluid from the surgical site at a first predetermined rate, wherein the fluid pump system intermittently operates in conjunction with a surgical tool which, when operational, removes fluid from the surgical site at a second predetermined rate greater than the first predetermined rate; a sensor for sensing a predetermined parameter of the surgical tool and providing an output signal indicating that the surgical tool is operating; and an actuating means responsive to the output signal to actuate the second fluid pump to remove fluid from the surgical site at the second predetermined rate.

13 Claims, 11 Drawing Sheets

Related U.S. Application Data division of application No. 15/077,348, filed on Mar. 22, 2016, now Pat. No. 10,369,270, which is a division of application No. 14/061,922, filed on Oct. 24, 2013, now Pat. No. 9,308,315, which is a division of application No. 11/642,457, filed on Dec. 20, 2006, now Pat. No. 8,591,453.

(52) U.S. Cl.
CPC ............... *A61M 2205/3331* (2013.01); *A61M 2205/3344* (2013.01); *A61M 2205/50* (2013.01); *A61M 2205/6081* (2013.01)

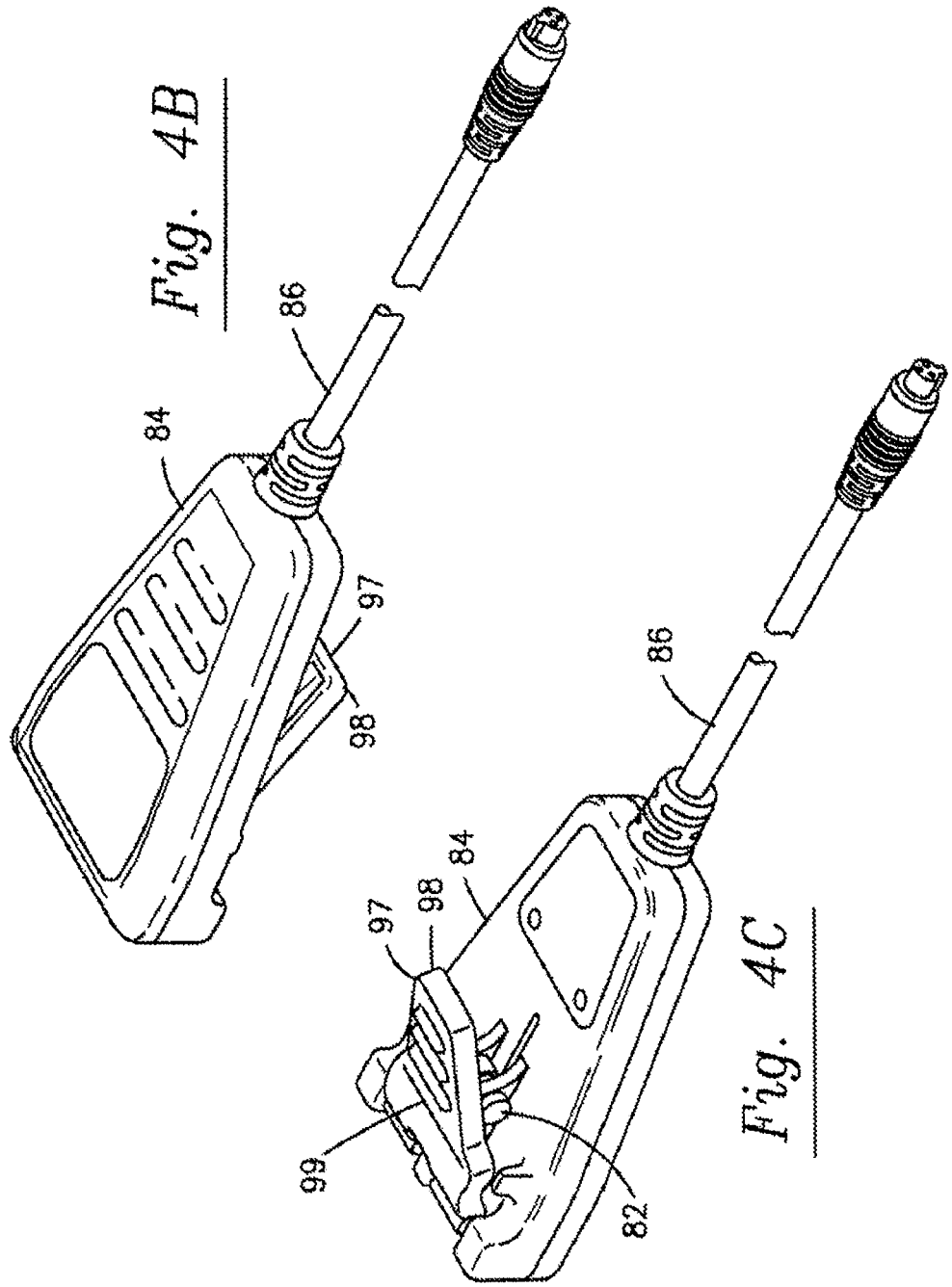

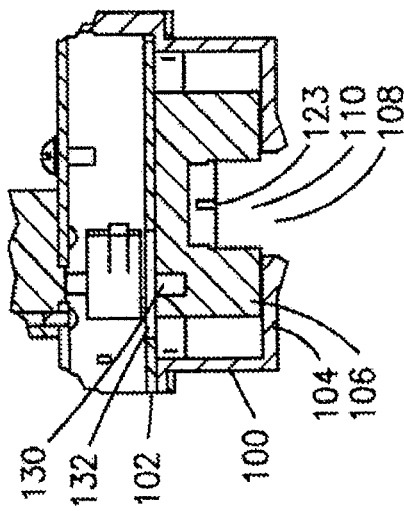
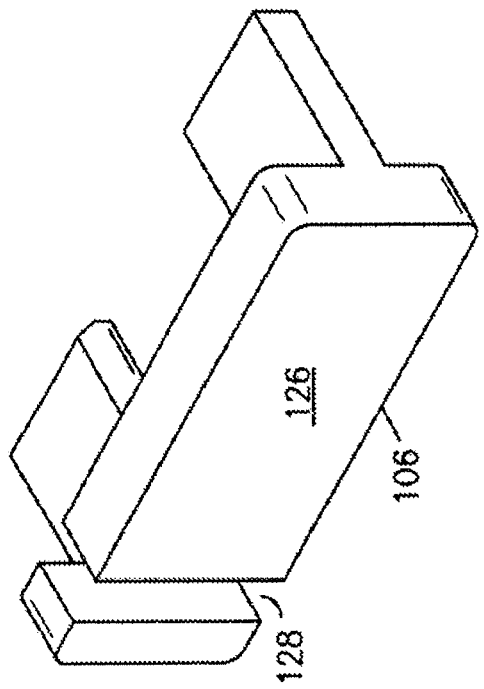
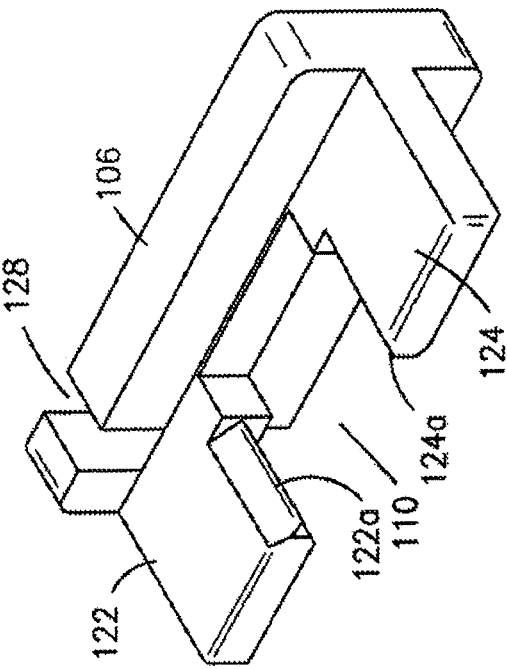

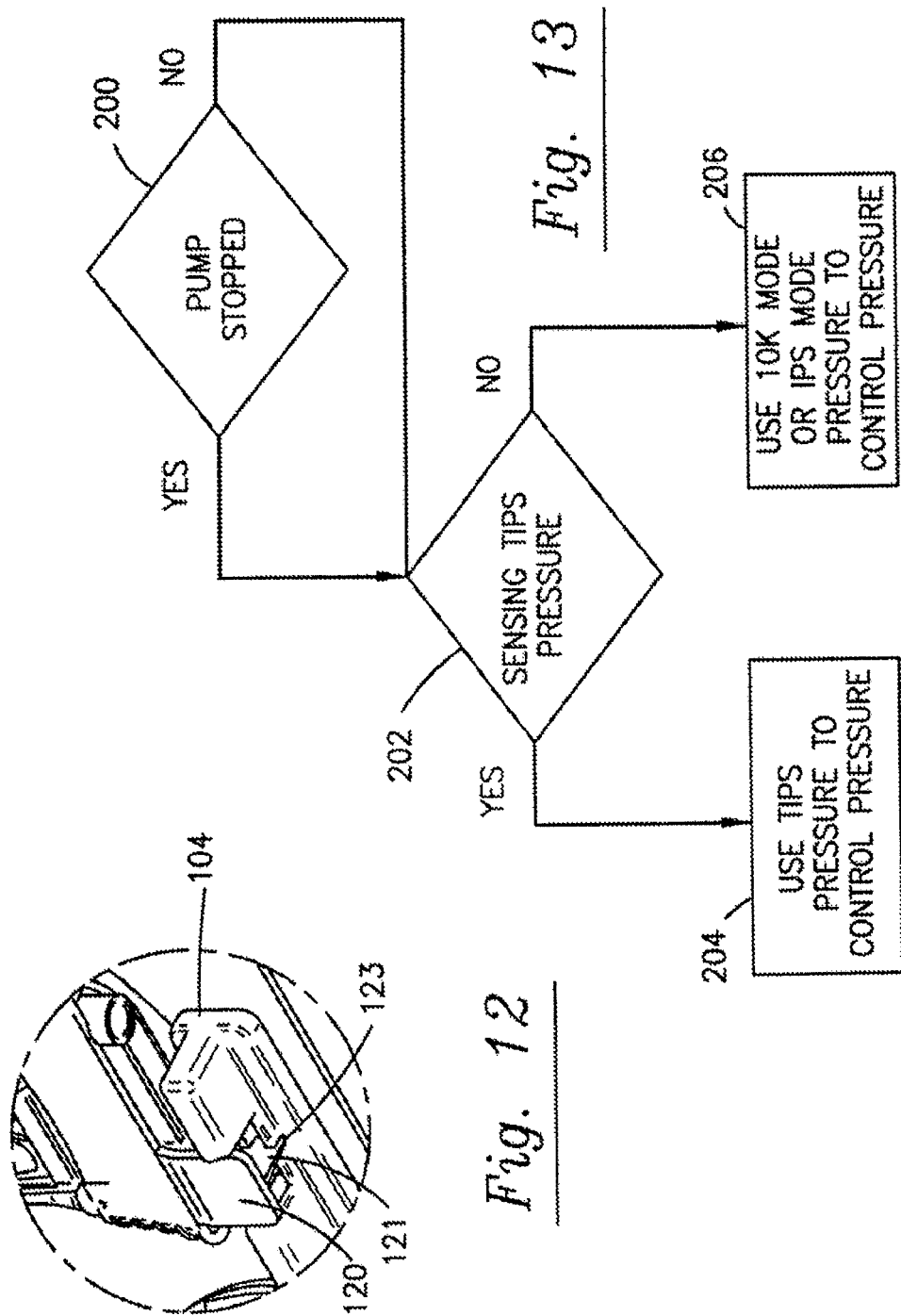

DUAL PUMP ARTHROSCOPIC IRRIGATION/ASPIRATION SYSTEM WITH OUTFLOW CONTROL

CROSS-REFERENCE TO RELATED APPLICATIONS

This application is a divisional of U.S. patent application Ser. No. 16/448,141, filed Jun. 21, 2019, now U.S. Pat. No. 11,602,590, which is a divisional of U.S. patent application Ser. No. 15/077,348, filed on Mar. 22, 2016, now U.S. Pat. No. 10,369,270, which is a divisional of U.S. patent application Ser. No. 14/061,922, filed on Oct. 24, 2013, now U.S. Pat. No. 9,308,315, which is a divisional of U.S. patent application Ser. No. 11/642,457, filed on Dec. 20, 2006, now U.S. Pat. No. 8,591,453.

FIELD OF THE INVENTION

The invention relates to systems for the irrigation and/or aspiration of fluids into or from a surgical work site during an endoscopic procedure. More particularly, the invention relates to a multi-purpose irrigation/aspiration system for use during minimally invasive surgery for the purpose of performing any one of a variety of irrigation/aspiration functions such as, for example, tissue lavage, joint distension or uterine distension. Still more particularly, the invention relates to an irrigation/aspiration system having a common control system operating two separate pumps, one pump dedicated to irrigation and one pump dedicated to aspiration. Still more particularly the invention relates to controlling the outflow fluid when an aspirating surgical tool is used with the system.

BACKGROUND OF THE INVENTION

Minimally invasive surgery also referred to herein as endoscopic surgery, often utilizes an irrigation system to force suitable biocompatible fluid into the area surrounding the surgical work site within a patient. The term "irrigation" is used broadly to mean any type of pressurized fluid flow whether it be for irrigation in particular or for other uses described below. Flexible plastic tubing is used to conduct the fluid from a source to the work site and from the work site to a drain or other receptacle. Flexible tubing is also sometimes used as a pressure monitoring line to convey fluid pressure information to a control mechanism. Depending upon the procedure, the irrigating fluid is useful for various purposes such as tissue lavage, hydro-dissection, joint distension, uterine distension, etc. Known irrigation systems include electrically driven pump systems, in which a suitable fluid is pumped through flexible tubes from a source to the work site, gravity-feed systems, in which the pump is replaced by merely adjusting the height of the fluid supply above the patient, and nitrogen powered systems.

Irrigation systems generally utilize a means to set the pressure desired at the surgical work site. A feedback loop uses information from a pressure sensor to maintain the set pressure within a desired range. The invention described herein includes improvements in pressure control.

Known aspiration systems employ a source of reduced-pressure (i.e. lower than that of the work site) and include vacuum systems, in which a vacuum source is simply connected via flexible tubes to the work site, and simple gravity controlled drain lines. Aspiration of the fluid serves to either simply remove it to improve visibility, prevent undesirable fluid accumulation or high pressure at the work site, or to regulate the flow rate to maintain a predetermined fluid pressure at the work site.

Because the irrigation and aspiration functions are commonly used together, prior art irrigation/aspiration systems have been developed to perform both functions with one system, often combined in one console which provides power and control. The irrigation system is generally used in conjunction with an aspiration system which removes the fluid pumped into the work site at a controlled rate depending on the flow rate selected by the surgeon. Dual pump irrigation and aspiration systems are known where one pump is dedicated to the irrigating function and another pump is dedicated to the aspirating function. Each system utilizes a collection of flexible tubes to connect the fluid and vacuum sources to appropriate instruments inserted into the body. The collection of tubes includes a fluid inflow conduit, a fluid outflow conduit and, in some instances, a pressure monitoring conduit. All of the tubes are packaged together as a tubing set and each tubing set is produced as a unit containing all necessary tubes and connections required for performing a particular procedure with a particular system. This invention relates to improvements in dual pump irrigation/aspiration systems.

Consequently, it is an object of this invention to produce an irrigation/aspiration system having an inflow pump and an outflow pump and a control system for operating each pump in accordance with predetermined characteristics defined for use during a selected one of several different surgical procedures.

It is also an object of this invention to produce a multi-purpose irrigation/aspiration system capable of operating with a variety of specific types of tubing sets, each set intended for use only during a particular type of surgical procedure.

It is also an object of this invention to produce a multi-purpose irrigation/aspiration system capable of operating with a variety of specific types of tubing sets which are each identified with a particular coding means associated with that tubing set type to identify the use for which the tubing set and/or the system associated therewith is intended.

It is also an object of this invention to produce two tubing cassettes for use with a multi-purpose irrigation/aspiration system wherein one cassette is dedicated to and facilitates the engagement of the irrigation tubing with the system and the other cassette is dedicated to and facilitates the engagement of the aspiration tubing with the system.

It is still another object of this invention to produce a dual pump irrigation/aspiration system having a flow control system which automatically changes the outflow of fluid based on whether another tool, such as a shaver blade handpiece is activated to withdraw additional fluid from a surgical work site.

It is yet another object of this invention to produce a dual pump irrigation/aspiration system having varying size peristaltic rollers and associated tubing cassettes to facilitate proper assembly.

It is also an object of this invention to produce a dual pump irrigation/aspiration system having a flow control system capable of controlling selectively pressure and flow on the basis of actual intra-articular pressure or a calculated/inferred pressure.

It is also an object of this invention to produce a dual pump irrigation/aspiration system having a valve means and a control for the valve means capable of drawing outflow fluid from selected outflow tubes.

It is yet another object of this invention to produce a dual pump irrigation/aspiration system having a software driven declogging feature.

SUMMARY OF THE INVENTION

These and other objects of this invention are achieved by the preferred embodiment disclosed herein which is a dual pump multi-purpose irrigation/aspiration pump system. The system is designed with a first pump to pump fluid from a source of irrigating fluid and a second pump to provide a source of aspirating vacuum during an endoscopic surgical procedure at a surgical work site. The system comprises a common console and a pump flow control system for controlling both a peristaltic inflow pump and a peristaltic outflow pump. The flow control system utilizes inflow and outflow pressure sensors and inflow and outflow flow rate controls. A tubing set comprising an inflow cassette housing, an outflow cassette housing and a plurality of flexible conduits is used to connect the source of irrigating fluid and aspirating vacuum to the surgical work site. The tubing set contains inflow and outflow pressure transducers and connects them to pressure sensors in the console. The tubing set is adapted for use during a predetermined type of surgical procedure and contains a coding means which carries a code to identify the type of surgical procedure and selected predetermined fluid pressure and flow characteristics associated therewith. Decoding means is provided on the console for reading the coding means to determine the code. Retention means is provided for receiving and holding the tubing cassettes and operatively engaging them and portions of the flexible conduits with their respective (inflow or outflow) pump, the flow rate control means and the decoding means. Also provided is a control means responsive to the code and the pressure sensors for controlling the inflow and outflow fluid pressures and flow rates in accordance with the predetermined characteristic identified by the code.

A further aspect of this invention is embodied in a system using two tubing cassettes, each for use with a respective one of the irrigation/aspiration pumps accessible on a single power/control console. The tubing cassettes comprise an inflow cassette housing which holds a first flexible tube for supplying irrigation fluid from a fluid source to the surgical work site and an outflow cassette housing which holds a second flexible tube for communicating a vacuum created by the outflow pump to the surgical work site. Additionally, the cassettes may also be provided with pressure transducers for communicating pressure data from inflow and outflow pressure transducers to pressure sensors on the console. The cassette housings for receiving the tubes comprise a code carrying means. The tubing cassettes are adapted to automatically align predetermined parts of the housing, code means and tubes with associated parts of the system console.

In one aspect of this invention a fluid pump system is provided for supplying fluid to and removing fluid from a surgical site, the system comprising a first peristaltic pump for supplying fluid, the first peristaltic pump having a roller assembly of a first predetermined diameter, and a second peristaltic pump for removing fluid, the second peristaltic pump having a roller assembly of a second predetermined diameter, the second predetermined diameter not equal to the first predetermined diameter.

Another aspect of this invention is an improvement in a fluid pump system which has a first fluid pump for pumping fluid from a source to a surgical site and a second fluid pump for removing fluid from the surgical site at a first predetermined rate wherein the fluid pump system intermittently operates in conjunction with a surgical tool which, when operational, removes fluid from the surgical site at a second predetermined rate greater than the first predetermined rate. The improvement comprises a sensor for sensing a predetermined parameter of the surgical tool and providing an output signal indicating that the surgical tool is operating. The improvement further comprises an actuating means responsive to the output signal to actuate the second fluid pump to remove fluid from the surgical site at second predetermined rate.

Another aspect of this invention is an improvement in a fluid pump system which has a first fluid pump for pumping fluid from a source to a surgical site and a second fluid pump for pumping fluid from the surgical site to a fluid drain and for removing fluid from the surgical site at a first predetermined rate, wherein the fluid pump system intermittently operates in conjunction with a surgical tool which, when operational, removes fluid from the surgical site at a second predetermined rate greater than said first predetermined rate. The improvement comprises a first input tube joining the surgical site to the second pump and a second input tube joining the surgical tool to the second pump and a shuttle means for alternatively pinching one or the other of the first and second input tubes, or neither tube. The shuttle means comprises a movable pinching member, moving means for moving the movable pinching member between a first position in which neither of the first or second tubes is closed, a second position in which only the first input tube is closed and a third position in which only the second input tube is closed. The improvement also comprises a control means for sensing the position of the moving means and for producing signals alternatingly representing the first, second and third positions.

Another aspect of the invention is a method for determining the pressure at a surgical work site in a variety of ways. Various pressure data sources are provided and a selected source is used in the feedback control loop to maintain the set pressure within a predetermined range. The system determines which pressure data sources are available and compares data to determine reliability of the data before selecting the pressure data source to be used. More specifically the invention includes a method for determining the pressure at a surgical work site during an endoscopic surgical procedure utilizing a fluid inflow pump, inflow tubing and an inflow cannula for conveying fluid from a fluid source to the surgical work site and a fluid outflow pump, outflow tubing and an outflow cannula for conveying fluid from the work site to a drain. The method further utilizes a pressure feedback control loop intended to maintain fluid pressure at the surgical work site at a pressure set point by determining actual pressure at the surgical work site and adjusting pressure and flow parameters to maintain the actual pressure at or near the set point pressure. The method comprises the steps of providing a first pressure determining means comprising a pressure sensor near the inflow pump to measure actual pressure at the output of the inflow pump; selectively providing a second pressure determining means comprising a pressure sensor at the surgical work site to measure actual pressure in the joint and providing a third pressure determining means comprising a joint pressure inferring system to calculate the actual pressure at the surgical work site using known and measurable pressure and fluid flow characteristics. The method further comprises selecting either the first, second or third pressure determining means as the source of the actual joint pressure to be used in the feedback control loop. The method may include the step of determining if a signal indicative of pressure is present at the surgical work site and, if so, using such signal to control operation of the pump.

In yet another aspect of the invention the irrigation/aspiration system is provided with a means for declogging a surgical tool which may suffer a blockage. More specifically, this declogging feature is included within a fluid pump system having a first fluid pump for pumping fluid from a source to a surgical site and a second fluid pump for removing fluid from the surgical site at a first predetermined rate. The fluid pump system intermittently operates in conjunction with a surgical tool which, when operational, removes fluid from the surgical site at a second predetermined rate greater than the first predetermined rate. The declogging feature comprises the method of removing a blockage in the outflow fluid path of the surgical tool wherein the method comprises the steps of producing a declogging signal, communicating the declogging signal to the fluid outflow pump to thereby cause the pump to reverse flow direction for a predetermined period of time and subsequently to return to operation in the forward direction for a different predetermined time. During the period of reversed flow, the surgical tool may be withdrawn from the work site so the clog may be directed to a waste container.

BRIEF DESCRIPTION OF THE DRAWINGS

FIGS. 4B and 4C are top and bottom perspective views of the shaver sensor shown schematically in FIG. 4A.

FIG. 5 is a cross-sectional view of FIG. 1 taken along the line A-A and omitting certain components for clarity.

FIG. 6 is a front perspective view of a slidable shuttle valve member.

FIG. 7 is a rear perspective view of FIG. 6.

FIG. 12 is a bottom perspective view of a portion of FIG. 1 showing portions of the outflow cassette and shuttle valve.

FIG. 13 is a flowchart of a portion of the control system incorporated into the console of FIG. 1.

DETAILED DESCRIPTION

Figure 1:
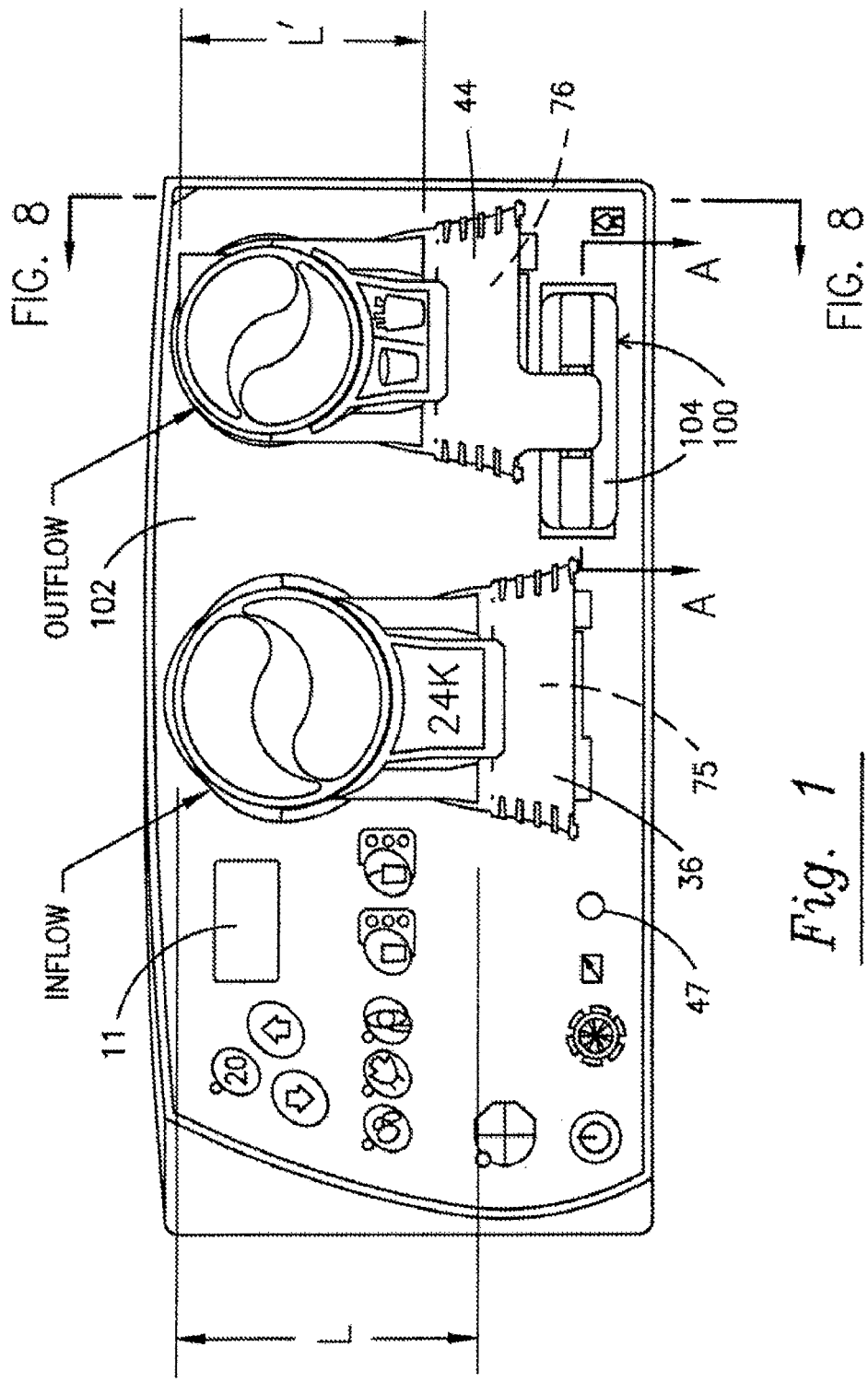
FIG. 1 is a front elevation view of a dual pump irrigation/aspiration console constructed in accordance with the principles of this invention.
Figure 2:
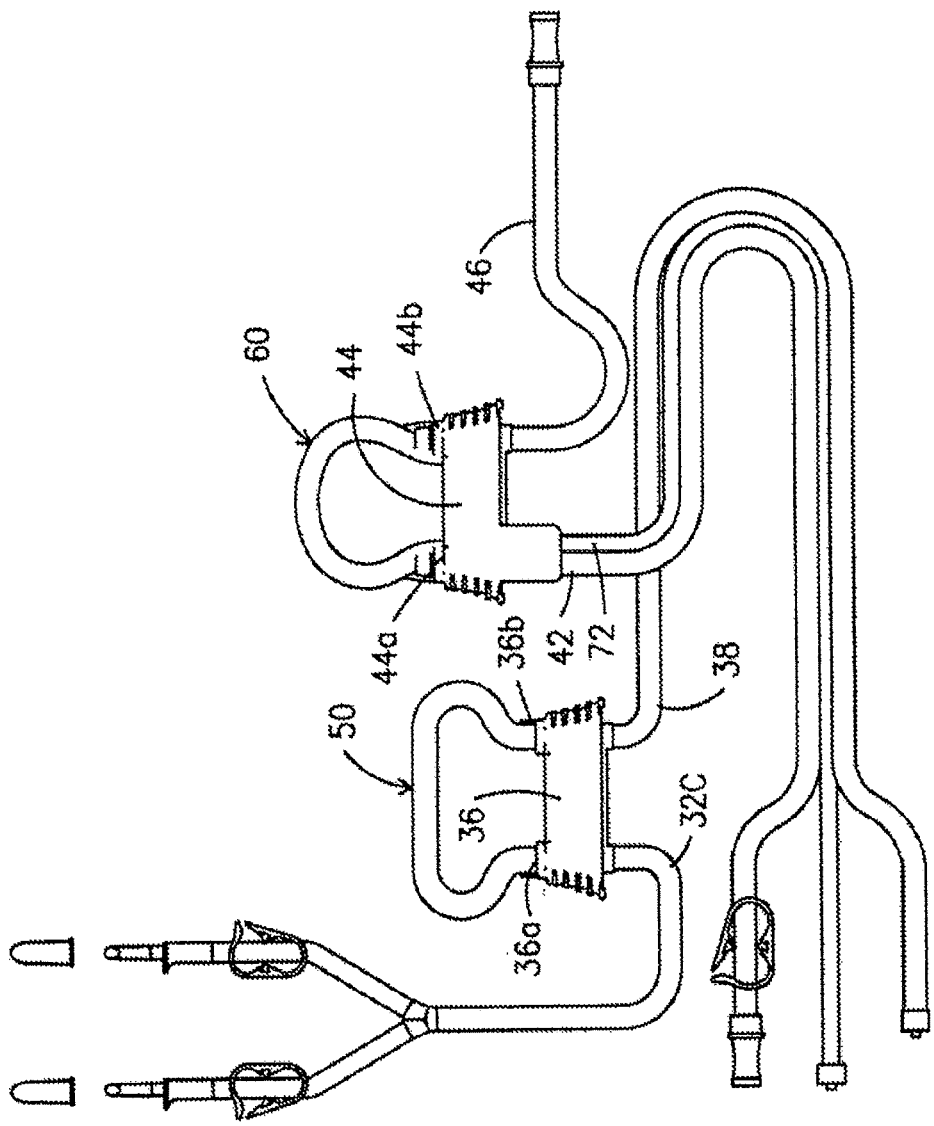
FIG. 2 is a schematic view of the tubing set for use with the console of FIG. 1.
Figure 3:
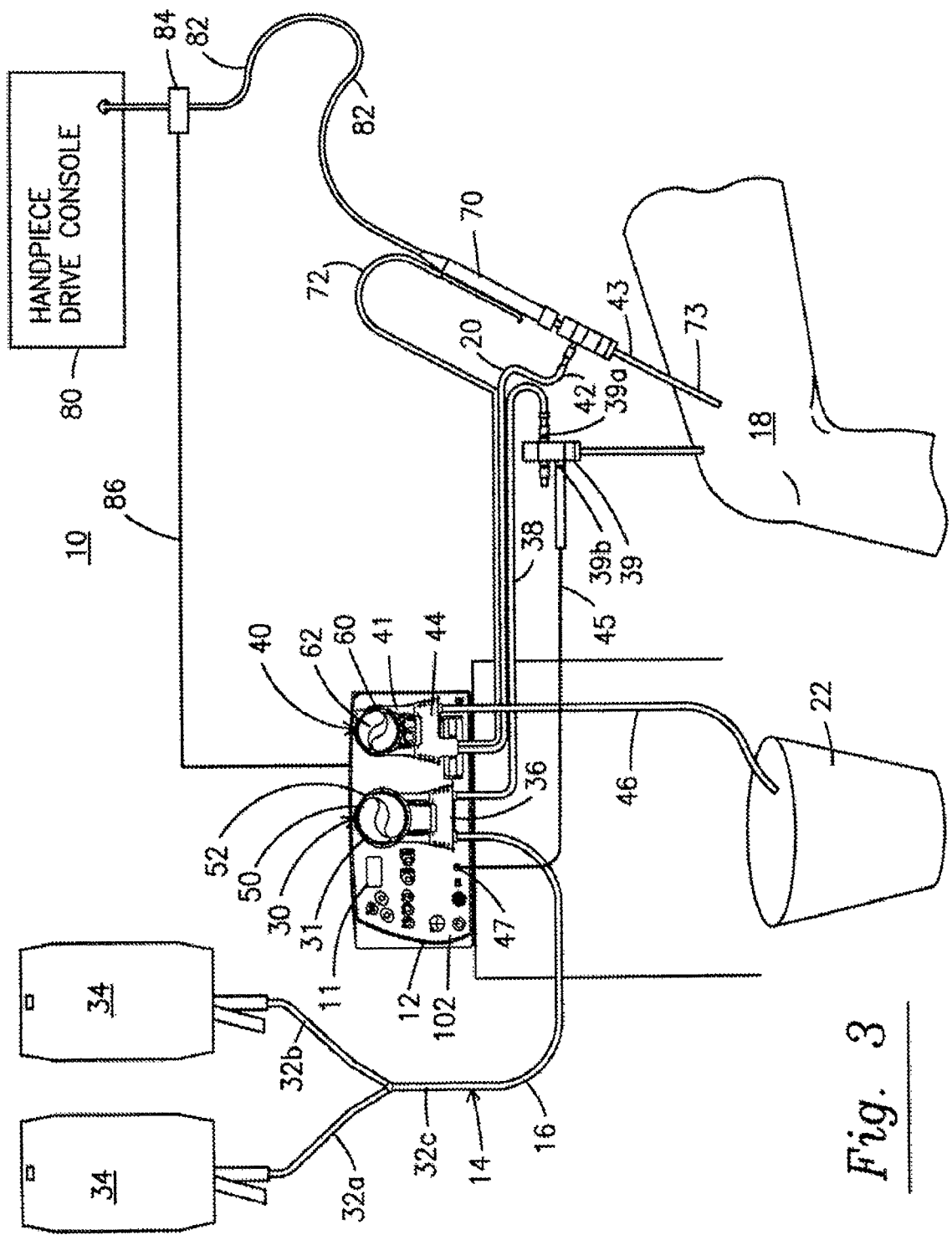
FIG. 3 is a view of the console of FIG. 1 assembled with the tubing set of FIG. 2 and connected for use during an arthroscopic procedure.
Figure 4A:
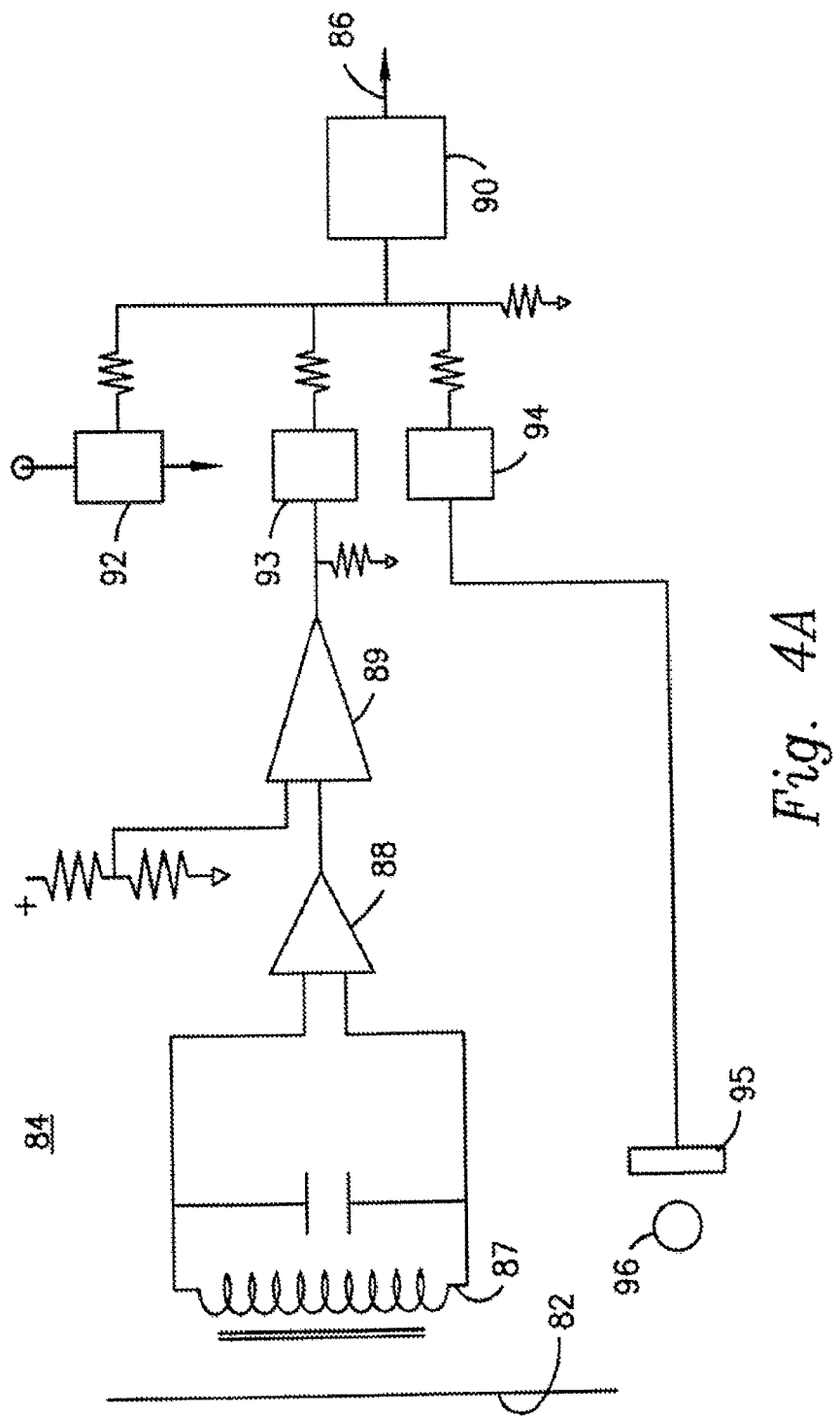
FIG. 4A is a schematic diagram of the shaver sensor component of the system.

Referring now to FIGS. 1 and 2 there is shown an exemplary dual pump irrigation/aspiration system 10 constructed in accordance with the principles of this invention and comprising pump console 12 and tubing set 14. Pump system 10 is adapted to deliver irrigating fluid from a fluid source to a surgical work site, at a selected pressure and flow rate, in an exemplary set up as shown in FIG. 3. The pump is suitable for use during a variety of selected surgical procedures and is, therefore, designed to be operable over a wide range of pressure and flow as selected by the user on control panel display 11 by up/down pressure control buttons to set desired pressure and up/down flow rate control buttons to set desired flow. After being set, display 11 can show actual pressure and/or flow. In the preferred embodiment, the pressure is selectable in 5 mm Hg increments between approximately 0 and 150 mm Hg. The inflow flow rate is selectable between approximately 0 and 2,500 ml/min (milliliters/minute) in the laparoscopic mode and in discrete amounts of 50, 100 or 150 ml/min in the arthroscopic mode (with the outflow flow rate also being 50, 100 or 150 ml/min respectively). As will be understood below, the rates may increase when auxiliary devices are used to remove a greater amount of fluid. Pressure and flow rate are both controlled by a flow control system incorporated into system 10, the flow control system being microprocessor controlled and menu-driven. Pump console 12 and tubing set 14 serve to communicate fluid from source 34 via irrigation or inflow tubing 16 to the work site 18 and from the work site via aspiration or outflow tubing 20 to a drain 22. Pump console 12 comprises an inflow peristaltic pump 30 and an outflow peristaltic pump 40.

Tubing set 14 comprises a plurality of elongated flexible conduits (such as polyvinyl chloride (PVC) tubes) which are retained in predetermined relationships to each other by cassettes 36 and 44 (described below) situated at points intermediate the ends of the various tubes of the tubing set. Tubing cassettes 36 and 44 of the present invention facilitate the engagement of the tubing set to the console 12 by holding intermediate peristaltic roller tubes 50 and 60, respectively, in predetermined open loop shapes (where the ends of the tubes are attached to laterally spaced bores on the cassette housings). This enables the user to easily and one-handedly place the two cassettes into position at their respective cassette receiving stations on pump console 12. Tubing set 14 is representative of a disposable tubing set usable with pump system 10. Each tubing set may be associated with a particular procedure and may have a differently colored cassettes or cassette labels and each separate tube attached to each cassette could be identified by different colors or markings to facilitate hooking up the system to the patient and fluid supplies. The different colors or other indicia could indicate that the code associated with the tubing set causes the system to be programmed to automatically limit flow and pressure ranges depending upon the procedure for which the tubing set is designed.

Tubing set 14 comprising inflow tubing 16 and outflow tubing 20. Inflow tubing 16 comprises inflow tubes 32a, 32b and 32c, inflow cassette 36 and inflow tube 38. Tubes 32a, 32b and 32c provide for communicating fluid from fluid source(s) 34 to inflow tubing cassette 36 attached to the inflow peristaltic pump 30 and then to inflow tube 38 connected to an endoscope sheath 39 or other appropriate inflow device to communicate the fluid to the work site 18. Outflow tubing 20 comprises a main outflow tube 42, outflow cassette 44, auxiliary outflow tube 72 and outflow tube 46. Outflow tube 42 is connected to a working cannula 43 and is adapted to provide a normal, relatively low flow fluid outflow path for fluid being aspirated from the work site 18. Auxiliary outflow tube 72 is adapted to provide increased fluid outflow from the work site 18 as will be understood below. Both outflow tubes 42 and 72 are connected to the outflow peristaltic pump 40 as will be understood below.

Inflow tubing 16 further comprises the aforementioned intermediate roller tube 50 (on inflow cassette 36) interposed between inflow tubes 32a and 38. Cassette 36 and roller tube 50 are adapted to engage inflow peristaltic pump 30 at an inflow cassette receiving station 31 on the front of pump console 12. Outflow tubing 20 further comprises outflow cassette 44 which is adapted to hold the aforementioned intermediate roller tube 60 interposed between outflow tubes 42/72 and 46. Outflow cassette 44 and outflow intermediate roller tube 60 are adapted to engage outflow peristaltic pump 40 at an outflow cassette receiving station 41. Each cassette 36 and 44 is provided with a pressure transducer member on its rear surface. Both cassette receiving stations 31 and 41 have pressure sensors 75 and 76, respectively, on front panel 102 behind cassettes 36 and 44, respectively, as best seen in FIG. 1. The sensors 75 and 76 are adapted to read the pressure when the associated cassette is properly installed.

The operation and structure of cassettes 36 and 44 and pressure sensors 75 and 76 is best understood by reference to U.S. Design Pat. 513,801 (Stubkjaer) issued Jan. 24, 2006, U.S. Design 513,320 (Stubkjaer) issued Dec. 27, 2005 and U.S. Ser. No. 10/701,912 (Blight et al.)(Publication No. US2005/0095155), filed Nov. 5, 2003, all assigned to the assignee hereof and incorporated by reference herein.

Different Size Pump Heads

Cassettes 36 and 44 facilitate the attachment of tubing set 14 to the input and output peristaltic pumps 30 and 40, respectively. In the preferred embodiment the cassettes are further improved over the aforementioned references by making the sizes of certain components on the inflow side of the system different from the sizes on the outflow side to avoid improper installation of tubing set 14 on pump console 12. Attachment of the tubing improperly could create an unsafe situation. While size variations may be achieved in a variety of ways, in the preferred embodiment as best seen in FIGS. 1-3 the size of the loop formed by inflow intermediate roller tube 50 is different than the size of the loop formed by the outflow intermediate roller tube 60. The relative sizes of the roller assembly of each peristaltic pump are also different and adapted to fit on and work with the chosen loop size. The size of the inflow and outflow cassettes and the tube lengths, i.e. the distances along the intermediate roller tubes between the loop ends 36a and 36b, and 44a and 44b, respectively (i.e. the length of the roller tubes), is varied to assure that cassettes 36 and 44 can only be installed one way on their respective receiving station. Furthermore, inflow cassette 36 has a loop length L between the top of the peristaltic roller and the top of cassette 36 when the latter is installed at its cassette receiving station. Outflow cassette 40 has a similarly defined loop length L' at its receiving station. In the preferred embodiment the peristaltic rotor (roller assembly) of the inflow peristaltic pump 30 has a diameter (2.89 inches, 73.4 mm), larger than the rotor of the outflow peristaltic pump 40 (2.45 inches, 62.2 mm). The tube lengths of the intermediate roller tubes are chosen to avoid too little tension (i.e. too long a tube) or too much tension (i.e. too short a tube) on the rotor. In the preferred embodiment the inflow and outflow roller tubes 50 and 60 are made of 50A C-Flex® TPE from Consolidated Polymer Technologies, Largo, Florida, and each has an outside diameter of 0.440 inches (11.18 mm), an inside diameter of 0.305 inches (7.75 mm), and a wall thickness of 0.068 inches (1.73 mm). The inflow roller tube 50 is 8.75 inches (222.25 mm) long and the outflow roller tube 60 is 7.25 inches (184.15) long. These dimensions, when applied to cassettes having roller to cassette distances of L, approximately equal to 4.36 inches (110.74 mm), and L' approximately equal to 3.54 inches (89.92 mm) enable the cassettes to be properly installed one-handedly onto their respective receiving stations with an acceptable amount of force. In the preferred embodiment the rotors may also be color coded to match the proper inflow or outflow cassette to further facilitate proper installation. Additionally, the intermediate tubes 50 and 60 may also be color coded.

The loop and rotor size variations of the preferred embodiment have several advantages. Improperly reversing the inflow and outflow cassettes will be almost impossible since placing the larger loop on the smaller rotor (i.e. inflow cassette on outflow rotor) will not only be apparent to the user but will result in a failure to operate. The flexible intermediate tube will simply be too loose. Also, placing the smaller loop on the larger rotor (i.e. outflow cassette on inflow rotor) will also be apparent to the user because the intermediate tube will be stretched too tightly to operate properly, and the force required to place the outflow cassette on inflow rotor will be so high as to make it noticeable to the user that something is wrong. It has been found that there is a relationship between the force required to properly and easily place each cassette (using only one hand) at its respective cassette receiving station. For any given roller tube structure (i.e. diameter, wall thickness, length, etc.) the ratio of tube length to loop length is in the range of approximately 1.7 to 2.1, preferably about 1.9.

Shave Sensor and Shuttle Valve

During a surgical procedure a shaver blade handpiece 70 may be used within cannula 43 in conjunction with a shaver blade 73 to resect tissue and otherwise remove debris from the work site 18. The resected tissue and debris are aspirated from the work site 18 along with fluid via cannula 43 and main outflow tube 42. This fluid path is normally open and the fluid flows at a relatively low rate during the surgical procedure to maintain pressure at the site and to clear debris. However, when handpiece 70 is operating fluid is made to flow at a higher rate via auxiliary outflow tube 72. In the preferred embodiment of the invention, system 10 further comprises a means to identify when shaver handpiece 70 is operating so that the pump control system can automatically establish the higher rate of flow. This is accomplished by sensing a predetermined operating parameter of the handpiece and using this information to activate a fluid diverter.

As shown in FIG. 3, to use a shaver handpiece a handpiece drive console 80 is connected via power line 82 to handpiece 70. In the preferred embodiment a shaver sensor means 84 is used to sense operation of the handpiece by detecting a parameter associated with the power line attached to the handpiece. Sensor 84 is connected via signal line 86 to pump console 12. As will be understood below, sensor 84 via associated circuitry in pump console 12 identifies when the handpiece 70 is activated and therefore when the fluid flow rate through inflow cassette 36 and outflow cassette 44 must increase to compensate for the fluid withdrawn from the work site by handpiece 70.

As schematically shown in FIGS. 3, 4A, 4B and 4C, sensor 84 is removably mechanically clamped onto power cable 82, preferably near the console 80 end in order to place it outside of the sterile field, and includes a resonant circuit/antenna 87, an amplifier 89, a comparator 88 and oscillator 90. The signal detected by coil 87 is ultimately delivered to console 12 on signal line 86 as a frequency output of oscillator 90. The input to the oscillator comprises three switches 92, 93 and 94. Switch 92 is adapted to provide an input to oscillator 90 on the power-up of sensor 84 (i.e. connection to console 12). This causes the frequency output of oscillator 90 to be 10 kHz. Switch 93 is adapted to provide an input to oscillator 90 upon the application of power to power line 82, thus indicating the shaver handpiece 70 is running. This causes the frequency output of oscillator 90 to be 20 kHz. Switch 94 is adapted to provide an input to oscillator 90 upon receiving a signal from Hall sensor 95 representative of the presence of magnet 96 near the Hall sensor. Magnet 96 is located in a pivoting clamp 97, one end 98 of which is movable relative to a base 99 containing the Hall sensor. When the clamp is placed on power line 82 the magnet is no longer detected by the Hall sensor (thus leaving switch 94 open). Switches 93 and 94 are adapted to work together to provide a 30 kHz oscillator output. The 30 kHz output is used to increase the speed of inflow pump 30 and to turn outflow pump 40 to the high flow mode and to perform other necessary functions to accomplish this as will be understood below.

An advantage of sensor 84 is its ability to operate with a variety of shaver systems because it is easily attachable and detachable. The sensing circuit detects near-field radio frequency (RF) leakage (wide spectrum noise) generated by the shaver power line and is, therefore, compatible with all shaver systems (although the method works better with AC powered shavers.)

To achieve a high flow mode, in addition to increasing the flow rate through inflow cassette 36 the control signal from shaver sensor 84 is used to activate a fluid diverter in the form of a shuttle valve 100, best seen and understood by reference to FIGS. 1 and 5 through 12. Shuttle valve 100 is placed on the front panel 102 adjacent outflow cassette 44 at the point near where outflow tubes 42 and 72 enter a manifold (not shown) on outflow cassette 44. The manifold is an element having two fluid inputs and one common output which serves to join both tubes 42 and 72 to a common peristaltic outflow intermediate roller tube 60. The flow to the input side of intermediate roller tube 60 is controlled by passing both of the two fluid input tubes (i.e. outflow tubes 42 and 72) through shuttle valve 100.

Shuttle valve 100 is a pinch valve that operates by alternatingly pinching one or the other of the outflow tubes 42 or 72 closed. Shuttle valve 100 is accessible on the front panel 102 of pump housing 12 adjacent the outflow peristaltic pump 40. As best seen in FIG. 5, shuttle valve 100 is attached to the front panel 102 and comprises a hollow slide housing 104 extending away from front panel 102 and containing a sliding shuttle member 106. Housing 104 essentially provides a track within which shuttle member 106 can slidingly reciprocate. Housing 104 has a central opening 108 wide enough to receive both outflow tubes 42 and 72 when the outflow cassette 44 is loaded onto its cassette receiving station on the front of the pump housing 12. Sliding shuttle member 106 includes a central opening 110 also adapted to receive both outlet tubes 42 and 72.

The operation of shuttle valve 100 is best understood by reference to FIGS. 8 through 11. In each of these drawings the outflow tubes 42 and 72 have been omitted for clarity. It should also be understood that FIGS. 9A, 10A and 11A are plan views taken along the section line A-A in FIG. 1 while FIGS. 9B, 10B and 11B are front elevation views taken along the section line B-B in FIG. 8.

Figure 10A:
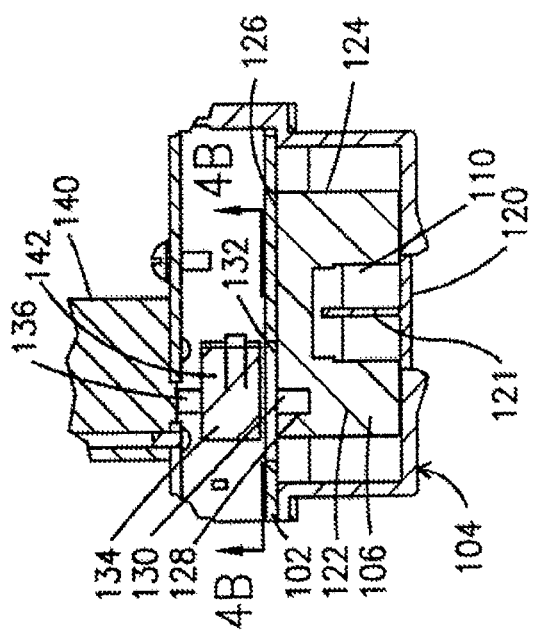
FIGS. 10a and 10b are plan and elevation views, respectively, of FIG. 5 showing the components in another state of operation.
Figure 11B:
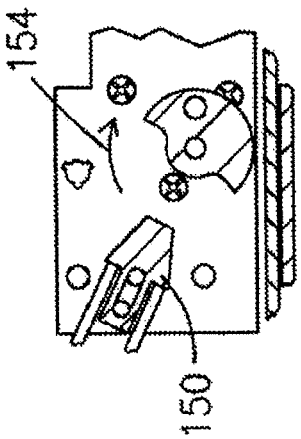

Referring first to FIG. 10A, it is noted that this view is identical to FIG. 5 except for the fact that FIG. 10*a* is a view with the outflow cassette 44 in place while FIG. 5 is a view with the outflow cassette 44 omitted. Outflow cassette 44 includes a cover tab 120 which is sized to cover openings 108 and 110 in the slide housing 104 and shuttle member 106 respectively. Tab 120 supports a backing plate 121 which extends perpendicularly from tab 120 toward front panel 102. Tab 120 is adapted to fit between outflow tubes 42 and 72 to facilitate selectively covering these tubes. As shown in FIG. 12, housing 104 is a shell generally conforming to the shape of shuttle member 106. The hollow base of housing 104 is notched at slot 123 to provide lateral support for the bottom of the distal end of backing plate 121. Housing 104 may be provided with a similar slot (not shown) to provide lateral support for the top of the distal end of backing plate 121.

In FIG. 5 shuttle member 106 is shown within slide housing 104 in a central position symmetrically situated around housing 104 opening 108 which is thereby aligned with shuttle 106 opening 110. As will be understood below, this position is automatically presented to the user upon start-up of system 10 in order to facilitate loading of tubing set 14. In this central position shuttle member 106 enables outflow cassette 44 to be loaded onto outflow peristaltic pump 40, as shown in FIG. 10A, with outflow tubes 42 and 72 both received within opening 110 of shuttle member 106 and tab 120 situated between the tubes (not shown). As will be understood below, shuttle member 106 is movable both to the left and right of the central position shown in FIG. 10*a*. As best seen in FIGS. 6 and 7 shuttle member 106 has a left body member 122 and a right body member 124 situated on either side of central opening 110, each member 122 and 124 having opposed and inwardly facing pinching surfaces 122*a* and 124*a* adapted to concentrate a squeezing force on outflow tubes 42 and 72, respectively, by alternatively pushing one tube or the other against backing plate 121. Shuttle member 106 has a rear surface 126 that can slide along the front panel 102, rear surface 126 having a vertical slot 128 at the rear of rear surface 126. Vertical slot 128 is adapted to engage a pin 130 extending through a rectangular slot 132 formed in front panel 102. Pin 130 is in turn attached to an arcuate cam 134 driven about its axis by a rotatable output drive shaft 136, driven in turn by shuttle drive motor 140. It will be understood that the rotating elements of this mechanism could be replaced by a linearly reciprocating mechanism or any other suitable device.

Figure 8:
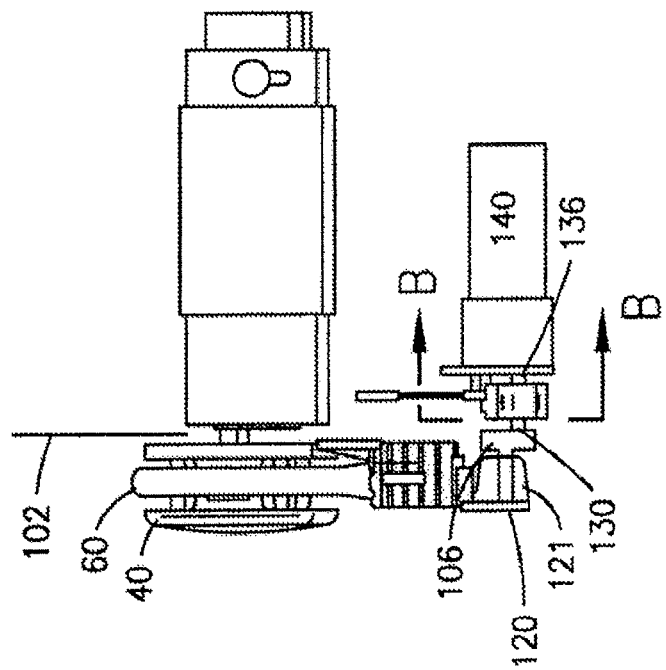
FIG. 8 is a cross-sectional view of FIG. 1 taken along the line 8-8 with certain components omitted for clarity.
Figure 10B:
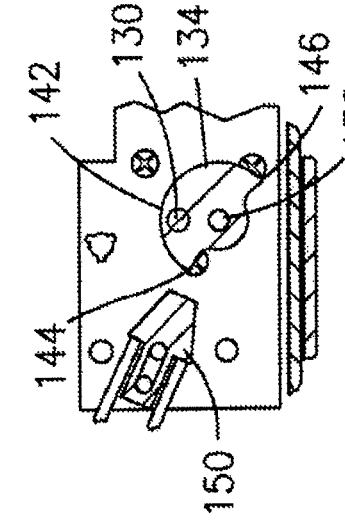

FIG. 10B shows the relationship of the components of FIG. 10*a* (taken along the line B-B of FIG. 8 at the point in time represented by FIG. 10A). Cam member 134 has a generally semi-circular profile and an outer partially cylindrical arcuate surface 142 situated at a fixed radius from the axis of drive shaft 136. Surface 142 terminates at opposite edges 144 and 146. An optical sensor 150, for example a light (or other radiation) emitting diode situated a predetermined distance from surface 142, is focused on surface 142 and adapted to sense the position of shuttle member 106 in a non-contact manner by detecting the presence and absence of surface 142 in the field of view of sensor 150. The shuttle member 106, cam member 134 and sensor 150 are physically correlated so that a given position of cam member 134 corresponds to define when the shuttle member is centered in the position shown in FIGS. 5 and 10A. In the preferred embodiment this correlation is achieved by having the shuttle member 106 in the central position shown in FIG. 10A when edge 144 of cam member 134 is situated so as to trigger a signal from sensor 150 that arcuate surface 142 cannot be detected. This 'no-detect" signal is equivalent to detecting edge 144 and indicates to the control system that the shuttle valve member 106 is in its central position thereby indicating that neither of the outflow tubes 42 and 72 is being pinched or occluded. This is the loading and unloading state of the system when neither peristaltic pump is operating.

Because of the clockwise direction of rotation of the peristaltic roller assemblies, the left side of each cassette 36 and 44 is the input side to its associated pump and the right is the output side of the pump. The input of inflow cassette 36 is provided only by single inflow tube 32c. However, as will be understood below, the input of outflow cassette 44 is provided by two sources: outflow tube 42 and outflow tube 72. As shown in FIG. 2, the exterior surfaces of these tubes may be physically joined to each other and to inflow tube 38 along a predetermined length to facilitate installation of tubing set 14. While outflow tubes 42 and 72 may be discrete tubes joined along their outer surfaces, they may also be a single tube (not shown) having two lumens. Each lumen would of course be joined by a suitable adapter (not shown) where necessary to connect the lumen to other components. For this reason, outflow tubes 42 and 72 are herein sometimes referred to as a dual lumen tube.

The shuttle control system incorporates a self-learning protocol on each start-up of console 12. This feature compensates for any reversal of the polarity of the wiring of motor 140 and determines the home or center position where the shuttle valve must be placed to enable loading and removal of tubing set 14. This feature operates as follows: (1) on startup a direction of rotation is arbitrarily selected and voltage of an arbitrary polarity is applied to motor 140 to drive it to one extreme of motion at which point current to the motor will increase; (2) at this point the output of detector 150 is determined (it will be either high or low depending upon whether surface 142 is detected or not); (3) the results of steps 1 and 2 are correlated in software and the system thus 'learns" that whatever extreme position (polarity) resulted from step 1 it is thereafter associated with the signal of step 2; (4) the opposite extreme position (polarity) is therefore automatically associated with the other possible signal of step 2. The zero, center position is then determined by simply reversing direction of the motor until the edge 144 crossover is detected.

Figure 9A:
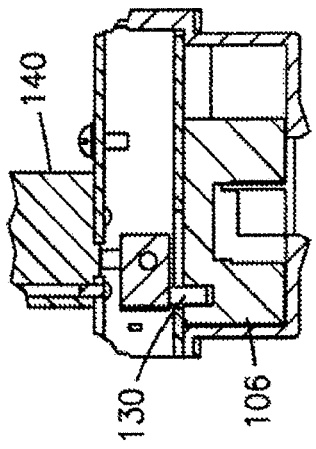
FIGS. 9a and 9b are plan and elevation views, respectively, of FIG. 5 showing the components in one particular state of operation.
Figure 9B:
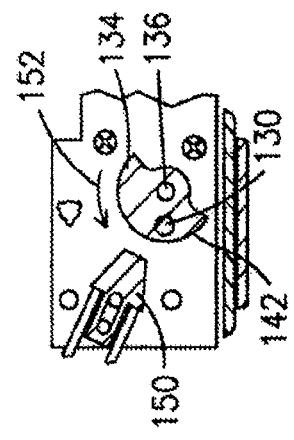
Figure 11A:
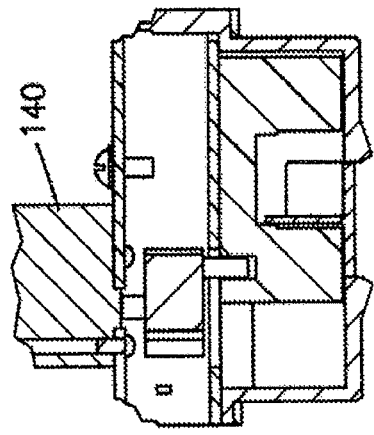
FIGS. 11a and 11b are plan and elevation views, respectively, of the components of FIG. 5 in yet another state of operation.

If at some point in the operation of pump console 12 there is detected the operation of an auxiliary device such as handpiece 70 (i.e. via an appropriate signal on line 86), the control system will interpret the signal from sensor 84 as a requirement to increase flow through shaver outlet tube 72 (the tube on the right side in FIG. 3 and on the right side of shuttle opening 110). This will result in a signal to motor 140 to move in direction 154 to the position associated with shuttle member 106 being in the right-most position as shown in FIG. 11a. If, however, it is determined desirable to continue drawing fluid from the left outlet tube 42 while pinching off the right outlet tube 72 (for example when shaver handpiece 70 is not running so oscillator 90 does not produce the 30 kHz signal), a signal is sent to motor 140 to rotate cam member 134 in direction 152. This will result in sensor 150 detecting the presence of cam surface 142, simultaneously moving pin 130 to the left thereby causing shuttle member 106 to move to the leftmost position as shown in FIG. 9b to leave open the left tube while pinching the right tube.

Inferred Pressure Sensing System

Pump system 10 utilizes a unique pressure sensing system to control the operation of inflow and outflow peristaltic pumps 30 and 40. System 10 monitors the pressure at the surgical site and increases or decreases fluid flow through tubing set 14 to maintain the surgeon requested pressure (i.e. set pressure) at the site while maintaining some outflow to clear debris, etc. from the site. As will be understood below the system uses sensed and/or calculated/inferred pressure information to adjust various parameters to maintain set pressure. The pump fluid control system can operate by receiving pressure information from either the inflow cassette sensor 75 alone, both inflow and outflow cassette sensors 75 and 76, or from a separate pressure sensing tube 45 attached to sensor port 47.

As shown in FIG. 3, tubing set 14 may be set up as a "one-connection" arthroscopic tubing set or as a "two-connection" arthroscopic tubing set. (In a "two-connection setup, optional tube 45 and pressure port 39b would be utilized, but in a "one-connection set-up they would not be utilized.) The term "one-connection" refers to the number of irrigating fluid and pressure sensing connections at the work site. A one-connection tubing set utilizes one fluid inflow line such as tube 38 to supply fluid to a work site during a surgical procedure and provides pressure information to the pump flow control system within the console via a pressure transducer attached to the fluid inflow line and operative with sensor 75 to produce a pressure value. In this case the pressure transducer is on the back of cassette housing 36 and sensor 75 is on front panel 102 adjacent cassette 36. Sensor 75 senses pressure in fluid tube 38 as described in the aforementioned Publication No. US 2005/0095155. As will be understood by those skilled in the art, in arthroscopic procedures, one-connection systems are used with a simplified inflow cannula or scope sheath which does not have a separate pressure sensing port. Alternatively, an optional "two-connection" tubing set could also be used. In this case scope sheath 39 is provided with a fluid inflow port 39a and a separate pressure sensing port 39b. The pressure sensing port 39b is connected via optional pressure sensing tube 45 to a pressure sensor/transducer 47 on pump console 12. A two-connection tubing set provides a way to determine pressure at the work site while a one-connection tubing set determines pressure at a given point in the fluid path. The pressure at the work site is herein referred to as True Intra-articular Pressure ("TIPS").

Since use of the TIPS system is optional, pump system 10 includes a method for determining the source of pressure information used to adjust the fluid flow and pressure produced by the system. Upon start-up, pump system 10 goes through a pressure determination sequence to identify the source of pressure data. As shown in the flowchart of FIG. 13, pump system 10 first determines at block 200 whether inflow pump 30 is operating (running) or not (stopped). In either case the sequence of events regarding identifying the source of pressure data is the same. If the pressure sensed by the inflow cassette sensor 75 is greater than a predetermined amount, chosen in the preferred embodiment to be 25 mm Hg, the control system will check at block 202 to see if sensor 47 is producing a signal, thus indicating the optional TIPS line 45 is being used. If the pressure is under the 25 mm Hg threshold the system will default to operating in the "10K" mode, i.e. with measured pressure data coming from sensor 75. If the measured pressure data exceeds the threshold and a TIPS signal is detected, block 204 will assure that the pump flow control system will continue to use this TIPS pressure data to control the operation of pump console 12. If no TIPS pressure signal is detected, block 206 will determine whether to use pressure data from the inflow cassette sensor 75 only (the 10K mode) or from an alternate known as the Inferred Pressure Sensing ("IPS") mode. The IPS system will only be used as a source of pressure data if (1) there is no TIPS signal at port 47 and (2) there is pressure data at both inflow cassette sensor 75 and outflow cassette sensor 76 and (3) there is a difference between the pressures sensed by the inflow and outflow cassette sensors 75 and 76.

The pressure values used by the pump flow control system are monitored such that if the TIPS or IPS pressure data fails or if the TIPS and IPS pressure values are significantly different (e.g. by an order of magnitude) the system will revert to the 10K mode for pressure information. The pump flow control system is a servo control loop using, as inputs to a proportional integral derivative (PID) comparator, a set point equal to the pressure selected by a user on control panel 102 and a feedback signal equal to the actual pressure measured by the system (i.e. from the 10K mode, TIPS or IPS).

The Inferred Pressure Sensing ("IPS") system is used to indirectly calculate pressure at the surgical site without measuring pressure directly as is done by the TIPS tubing. The IPS system produces a pressure value based on sensed pressure and calculated flow at certain points in the tubing set and calculating the effect of pressure drops associated with certain components of the set. The sensed and calculated/inferred values are used in various equations to arrive at a calculated value representative of the pressure at the surgical site without having to actually measure pressure at the site. The advantage of this is that it enables the system to provide increased pressure measurement accuracy even with a wide variety of cannulas of different sizes. The IPS system is a method of accounting for fluid flow drops and pressure losses and compensating for these drops and losses to thereby maintain a more accurate pressure at the surgical site.

The mathematical equation describing fluid flow and pressure drops through the various tubes of tubing set 14 is a complex polynomial, although it can be reduced in a first order approximation simply to $$P = R \times F \quad \text{(equation 1)}$$

where R=flow resistance, F=flow rate and P=pressure. This simplified expression is deemed valid because of the magnitude of flow in the surgical procedures involved (about 1 to 2 liters per minute) and because the control system will sample data at very short time intervals thereby approximating a static system, as will be explained below.

Figure 14:
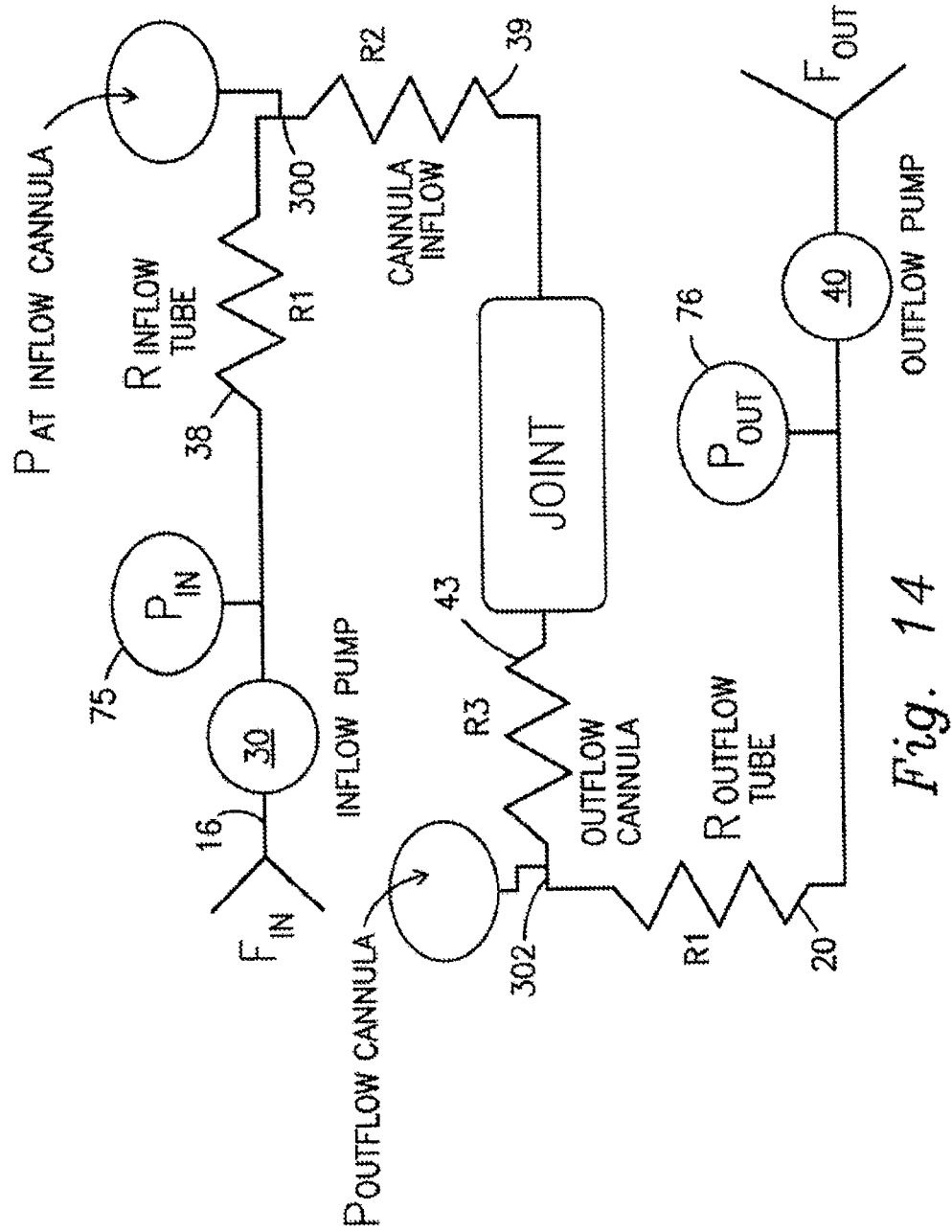
FIG. 14 is a schematic pressure/flow diagram describing various components of the system depicted in FIG. 3.

FIG. 3 has been redrawn as a pressure/flow diagram FIG. 14 to explain the IPS system and the application of the aforementioned equation to this IPS system. The components of FIG. 3 each have certain pressure, flow and resistance characteristics that are depicted schematically in FIG. 14. Thus, in FIG. 14 the following values are measured by the system: $P_{in}$, the inflow pressure sensed by cassette sensor 75 associated with the inflow cassette 36; $P_{out}$, the outflow pressure sensed by cassette sensor 76 associated with the outflow cassette 44; $F_{in}$, the inflow fluid flow rate going into the work site 18 as determined by an encoder (not shown) adapted to calculate the fluid volume moved by inflow peristaltic pump 30 per unit of time; and $F_{out}$, the outflow fluid flow rate coming out of the work site as determined by a similar encoder (not shown) adapted to calculate the fluid volume moved by outflow peristaltic pump 40 per unit of time. Those skilled in the art will understand that the flow rates can be determined as a function of the inner diameter of the intermediate roller tubes, the distance between the rollers of the peristaltic rotor assemblies and the speed of rotation of the rotor assemblies. These pressure and flow values are known values which are sampled by the system at intervals such as 10 mm (in the preferred embodiment).

The remaining data needed to use the equation P=F×R is the flow resistance of the tubes and cannulas used in the set-up of FIG. 3.

To facilitate the explanation of FIG. 14 the various resistances are identified by the name of the component in the flow direction. Thus, the resistance $R_{inflow\ tube}$ is labeled with the subscript "inflow tube" because it is the resistance of tube 38, the inflow tube encountered by the fluid after pump 30. This resistance causes a pressure drop $P_{drop\ inflow}$ tube across the tube. The resistance $R_{inflow\ tube}$ is calculated during manufacture of system 10 and stored in memory. Thus, the pressure drop $P_{drop\ inflow}$ tube across tube 38 is known and $= F_{in} \times R_{inflow\ tube}$. Therefore, the pressure at the inflow port of cannula 39 (i.e. point 300) can now be calculated as $$P_{at\ inflow\ cannula} = P_{in} - P_{drop\ inflow\ tube}$$

which is rewritten as $$P_{at\ inflow\ cannula} = P_{in} - R_{inflow\ tube} \times F_{in}.$$

The fluid flowing through the inflow cannula undergoes a further pressure drop before reaching the joint so $$P_{at\ inflow\ cannula} - P_{drop\ inflow\ cannula} = P_{joint}.$$

We know the pressure drop across inflow cannula 39 is $$P_{drop\ inflow\ cannula} = R_{inflow\ cannula} \times F_{in}.$$

Therefore, $$P_{at\ inflow\ cannula} - (R_{inflow\ cannula} \times F_{in}) = P_{joint} \quad \text{(equation 2)}$$

At this point $R_{inflow}$ cannula is unknown.

On the outflow side, we know that $$P_{at\ outflow\ cannula} = P_{out} + P_{drop\ outflow\ tube}$$

and $$P_{drop\ outflow\ tube} = R_{outflow\ tube} \times F_{out}$$

where $P_{out}$ is the pressure sensed by sensor 76.

Consequently, the pressure at point 302 is $$P_{at\ outflow\ cannula} = P_{out} + (R_{outflow\ tube} \times F_{out}).$$

In the preferred embodiment, inflow tube 38 and outflow tube 20 are identical in length, inner and outer diameter and material composition and, therefore, $R_{outflow\ tube}$ is the same as Rinflow tube. We know that the pressure in the joint can be expressed in terms of the parameters at the outflow side as $$P_{joint} = P_{at\ outflow\ cannula} + P_{drop\ outflow\ cannula}$$

and therefore $$P_{joint} = P_{at\ outflow\ cannula} + (F_{out} \times R_{outflow\ cannula}) \quad \text{(equation 3)}$$

We know that $$F_{loss} = F_{in} - F_{out}$$

to account for leakage of fluid. Because the data sample rate is fast (in the range of approximately 1 to 20 ms, preferably approximately every 10 ms) we assume no fluid loss so that $$F_{in} = F_{out}.$$

Therefore, equation 2 may be rewritten as $$P_{at\ inflow\ cannula} - (R_{inflow\ cannula} \times F_{out}) = P_{joint} \quad \text{(equation 4)}$$

Combining equations 3 and 4 produces the following:

$$P_{at\ inflow\ cannula} - (R_{inflow\ cannula} \times F_{out}) = $$
$$P_{at\ outflow\ cannula} + (F_{out} \times R_{outflow\ cannula}) \quad \text{(equation 5)}$$

Rearranging equation 5 results in $$P_{at\ inflow\ cannula} - P_{at\ outflow\ cannula} = F_{out}(R_{outflow\ cannula} + R_{inflow\ cannula}) \quad \text{(equation 6)}$$

In the preferred embodiment the $R_{outflow\ cannula}$ is very low because outflow cannulas are designed to easily drain fluid from the work site. (As noted below, this explanation requires additional calculations if the outflow cannula is restrictive to any appreciable degree.) Additionally, the outflow flow rate is relatively low so the pressure drop is low. Thus, equation 6 is simplified to $$P_{at\ inflow\ cannula} - P_{at\ outflow\ cannula} = F_{out} \times R_{inflow\ cannula}$$

and $R_{inflow\ cannula}$ is now able to be determined as $$R_{inflow\ cannula} = (P_{at\ inflow\ cannula} - P_{at\ outflow\ cannula})/F_{out} \quad \text{(equation 7)}$$

$R_{inflow\ cannula}$ is now known. These results can now be used in equation 4 (since $P_{at\ inflow\ cannula}$ is known) to predict the pressure in the joint and regulate the control loop using inflow pressure data. Combining equation 7 and equation 4 results in $$P_{at\ inflow\ cannula} - (R_{inflow\ cannula} \times F_{out}) = P_{joint}$$

$$P_{joint} = P_{at\ inflow\ cannula} - F_{out}[(P_{at\ inflow\ cannula} - P_{at\ outflow\ cannula}/F_{out}]$$

$$P_{joint} = P_{outflow\ cannula}$$

These results predict the pressure in the joint using outflow pressure data. The results of the $P_{joint}$ calculation from the inflow side is compared to the $P_{joint}$ calculation from the outflow side. If there is any difference between the two, outside of a predetermined range, the system will revert to a different pressure sensing mode. If the results are within the predetermined range, the $P_{joint}$ calculated from the inflow side is used to control the joint pressure. It is noted that this method enables calculation of joint pressure through the use of calculated values and without the necessity for any direct measurements of the joint pressure. This solution holds for the simplest case where all assumptions made above are valid. Further calculations are necessary to account for a more restrictive outflow cannula than is used in the preferred embodiment.

Declogging

Pump system 10 also incorporates a declogging method for facilitating automatic removal of a blockage of the shaver aspirating tubing line 72. The declogging system comprises software driven steps which control the output pump 40 to activate this function.

The declogging feature operates during use of handpiece 70 by sensing various characteristics of the operation of system 10 to determine the likelihood of a clog. If the outflow peristaltic rotor is working and the inflow peristaltic rotor is not working (or if the inflow rotor speed is significantly less than the outflow rotor speed) and if pressure at the work site (or pressure at both cassettes) is not changing, it is probable that the shaver blade or aspiration line 72 is clogged. In this event, the user may activate a declog button (not shown) which causes the outflow rotor to be activated in the opposite direction for a time period sufficient to create a pressure pulse to move approximately 5-15 ml of fluid through outflow line 72, handpiece 70 and shaver 73. After this time period the outflow rotor resumes normal operation. In the preferred embodiment, 5-15 ml of fluid displacement is deemed sufficient for the size of the tubing used. Approximately 5 ml of fluid (approximately 6.2 inches (157.48 mm) long in a 0.25 inch (6.35 mm) internal diameter tube) is an estimate of a volume sufficient to move the fluid back to the clog, and another approximately 5 ml is an estimate of the fluid required to push the clog out. In use, the surgeon would remove the shaver from the work site and aim it at a waste container. The declog button would cause the outflow rotor to be run in reverse as quickly as possible for approximately three revolutions and then forward for approximately six revolutions to push the clog out.

Figure 15:
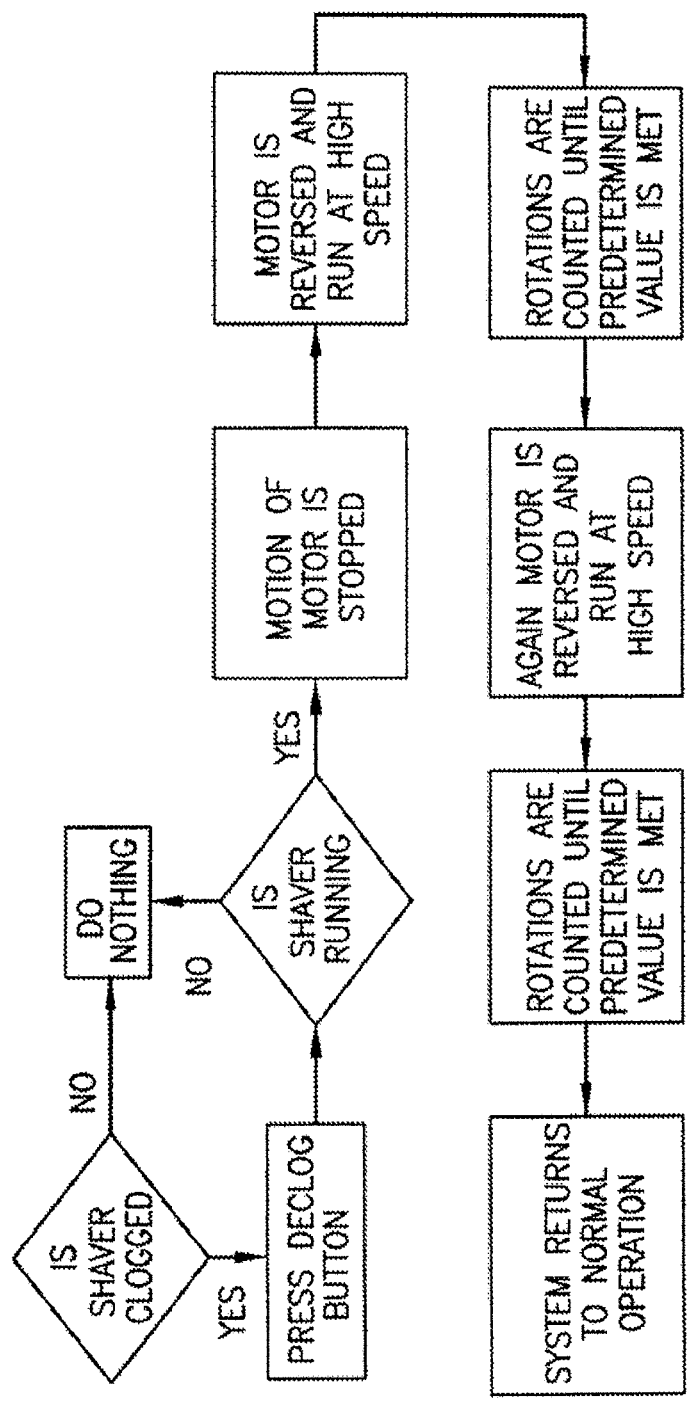
FIG. 15 is a flowchart of the declogging procedure portion of the control system used in the console of FIG. 1.

FIG. 15 is a flowchart describing the operation of the declogging feature.

It will be understood by those skilled in the art that numerous improvements and modifications may be made to the preferred embodiment of the invention disclosed herein without departing from the spitit and scope thereof.

What is claimed is:

1. A method for pressure sensing comprising the steps of:
providing a fluid pump system comprising: (i) a console having a first fluid pump for pumping fluid from a source to a surgical site and a second fluid pump for removing fluid from the surgical site at a first predetermined rate, wherein the fluid pump system intermittently operates in conjunction with a surgical tool which, when the surgical tool is operational, the surgical tool removes the fluid from the surgical site at a second predetermined rate greater than the first predetermined rate; (ii) a sensor for sensing a predetermined parameter of the surgical tool and providing an output signal indicating that the surgical tool is operating; (iii) a control system responsive to the output signal to actuate the second fluid pump to remove the fluid from the surgical site at the second predetermined rate; (iv) a first fluid inflow tube attached to a first transducer disposed within the first fluid pump, wherein the first fluid inflow tube is connected to a fluid inflow port; and (v) a scope sheath comprising the fluid inflow port and a pressure sensing port, wherein the pressure sensing port is connected to a second fluid inflow tube attached to a second transducer on the console;
powering the surgical tool through an electrical power cord;
detecting, by the sensor, the predetermined parameter which is associated with an electrical current flowing in the power cord, wherein the sensor is adapted to be situated adjacent to the power cord;
detecting operation of the first fluid pump and the second fluid pump wherein a pressure sensed by the first transducer is less than a predetermined amount; and
receiving pressure data from the first transducer.

2. The method of claim 1, further comprising the steps of:
detecting the operation of the first fluid pump and the second fluid pump wherein the pressure sensed by the first transducer is greater than the predetermined amount;
receiving a signal from the second transducer indicating the second fluid inflow tube is operational; and
receiving pressure data from the second transducer.

3. The method of claim 1, wherein the power cord extends between the surgical tool and the console.

4. The method of claim 1, further comprising the step of:
detecting, by the sensor, radio frequency emanations from the power cord.

5. The method of claim 1, wherein the sensor comprises a clamp for selectively engaging the power cord, the clamp comprising a base member and a holding member movable relative to the base member.

6. The method of claim 5, further comprising the step of:
engaging the power cord with the clamp when the base member and the holding member are in a first position relative to each other.

7. The method of claim 6, wherein the sensor comprises a first signal member in one of the base member or the holding member.

8. The method of claim 7, wherein the sensor comprises a second signal member in the other of the base member or the holding member.

9. The method of claim 8, further comprising the step of:
producing a first signal, by a cooperation of the first signal member and the second signal member, when the clamp is in the first position, wherein the first signal is representative of the surgical tool being turned on.

10. The method of claim 9, further comprising the step of:
producing a second signal, by the cooperation of the first signal member and the second signal member, when the clamp is in a second position, wherein the second signal is representative of the surgical tool being turned off.

11. The method of claim 10, wherein the first signal member is a magnet and the second signal member is a Hall sensor.

12. The method of claim 11, wherein the magnet is adjacent to the Hall sensor when the clamp is disengaged from the power cord.

13. The method of claim 12, wherein the magnet is removed from the Hall sensor when the clamp is engaged with the power cord.

* * * * *